(12) United States Patent
Nugent et al.

(10) Patent No.: US 7,507,838 B2
(45) Date of Patent: Mar. 24, 2009

(54) PROCESS FOR THE PREPARATION OF Z-5-CARBOXYMETHYLENE-1,3-DIOXOLAN-4-ONES

(75) Inventors: William A. Nugent, Wilmington, DE (US); Keming Zhu, Highland Park, NJ (US); James H. Simpson, Hillsborough, NJ (US); Edward J. Delaney, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 582 days.

(21) Appl. No.: 11/208,635

(22) Filed: Aug. 22, 2005

(65) Prior Publication Data

US 2006/0047129 A1 Mar. 2, 2006

Related U.S. Application Data

(60) Provisional application No. 60/606,606, filed on Sep. 1, 2004.

(51) Int. Cl.
*C07D 317/34* (2006.01)
(52) U.S. Cl. .................................... 549/296
(58) Field of Classification Search ............ 549/430, 549/435, 448, 453, 296
See application file for complete search history.

(56) References Cited

U.S. PATENT DOCUMENTS 6,777,440 B2 8/2004 Walker et al.

FOREIGN PATENT DOCUMENTS

WO WO 03/049690 A2 * 6/2003
WO WO 2004/004657 A2 1/2004

OTHER PUBLICATIONS

Dermer et al., "Methyl Esters and 1,3-Dioxolan-4-Ones Dervied From Simple Alpha-Hydroxy Carboxylic Acids", Proc. Okla. Acad. Sci., vol. 52, pp. 66-69 (1972).
Ferezou et al., "Total Synthesis of Avermectins, Part 1. Enantioselective Synthesis of the Southern Part Using a Sequential Dieckmann-free Radical Cyclization Approach", Bull. Soc. Chem. Fr., vol. 131, pp. 865-894 (1994).
Fischer et al., "Uber Acetonieren mit Aceton und Zinkchlorid", Chem. Ber., vol. 60, pp. 485-490 (1927).
Jarosz et al., "Reactivity and Crystal Structure of 1,2:3,4:5,6-Tri-O-isopropylidene-D-gluconolatone", Polish J. Chem., vol. 72, pp. 1182-1190 (1998).
Kneer et al., "Chiral Dienophiles Derived from Malic Acid: Synthesis of (Z)-(2S)-(tert-Butyl)-5-(ethoxycarbonylmethylene)-1,3-dioxolan-4-one and Its Diels- Alder Reaction with Cyclopentadiene", Synthesis, pp. 599-603 (1990).
Markert et al., "A Simple Approach to 5,5'-bis(1,3-dioxolan-4-ones) of Tartaric Acids", Tetrahedron: Asymmetry, vol. 15, pp. 803-806 (2004).
Ramage et al., "Dioxolanones as Synthetic Intermediates. Part 4. Biomimetic Synthesis of Multicolanic Acid", J. Chem. Soc. Perkin. Trans. I, pp. 1555-1560 (1984).

* cited by examiner

*Primary Examiner*—Bernard Dentz
*Assistant Examiner*—David E Gallis
(74) *Attorney, Agent, or Firm*—Burton Rodney

(57) ABSTRACT

A process for preparing Z-5-carboxymethylene-1,3-dioxolan-4-ones is provided which includes the steps of reacting a bis-ketal or bis-acetal of tartaric acid with a potassium containing base to form the carboxymethylene-1,3-dioxolan-4-one. A process for preparing HIV integrase inhibitors employing the carboxymethylene-1,3-dioxolan-4-one inhibitor is also provided.

16 Claims, No Drawings

PROCESS FOR THE PREPARATION OF Z-5-CARBOXYMETHYLENE-1,3-DIOXOLAN-4-ONES

FIELD OF THE INVENTION

This application claims a benefit of priority from U.S. Provisional Application No. 60/606,606, filed Sep. 1, 2004, the entire disclosure of which is herein incorporated by reference.

The present invention relates to a novel process for the preparation of Z-5-carboxymethylene-1,3-dioxolan-4-ones from a bis-ketal or bis-acetal of tartaric acid, which are intermediates in the preparation of HIV integrase inhibitors useful in the treatment of HIV, and to a process for preparing such HIV integrase inhibitors employing such intermediates.

BACKGROUND OF THE INVENTION

Z-5-Carboxymethylene-1,3-dioxolan-4-ones of formula A (where $R_1$ and $R_2$ can be independently H, alkyl or aryl) have been widely utilized as synthetic intermediates in Diels-Alder and free radical chemistry as well as in the preparation of HIV integrase inhibitors as disclosed in WO 2004/004657.

A process for preparing a compound of formula A ($R_1$, $R_2$=pentamethylene) is described by Ramage and McCleery in *J. Chem. Soc. Perkin Trans. I*, pages 1555-1560, 1984. This process utilizes a Wittig reaction between anhydrous tert-butyl glyoxylate and a heterocyclic phosphorane. However, this process is inefficient and not suitable for large scale manufacturing of compounds of formula A

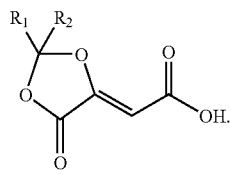

A

An improved procedure for the synthesis of compounds of formula A ($R_1$=tert-butyl, $R_2$=H) from S-malic acid is reported by Kneer et. al. in *Synthesis*, pages 599-603, 1990. This procedure utilizes acetal-protected malic acid B as starting material. Because malic acid is not in the correct oxidation state for direct conversion to A, it is necessary to carry out a bromination reaction. However, bromination of the free carboxylic acid results in extensive decarboxylation so that it is necessary to first convert the acid to an ester and then hydrolyze the ester at the end of the synthetic sequence. This fact, coupled with the limited selectivity of the bromination reaction, limits the efficiency of the overall process.

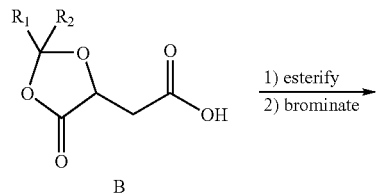

B

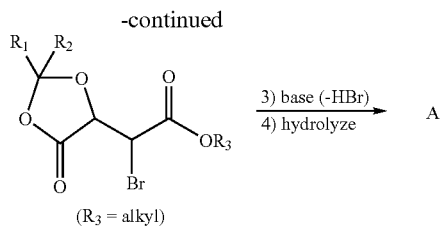

($R_3$ = alkyl)

In principle, the requirement for a bromination step would be circumvented by using a derivative of inexpensive tartaric acid as a starting material. Unlike malic acid, tartaric acid is already in the correct oxidation state to produce A via an elimination reaction. A suitable derivative for such a process would be the bis-ketal C. Preparation of such a compound was reported by Fischer and Taube in *Chem. Ber.*, Vol. 60, pages 485-490, 1927, who prepared C($R_1$=$R_2$=methyl) by the action of acetone on tartaric acid in the presence of either zinc chloride or hydrogen chloride. Subsequently an improved preparation of the same compound C was reported by Dermer and George in *Proc. Oklahoma Acad. Sci.* Vol. 52, pages 66-69, 1972, who utilized boron trifluoride as a catalyst. For the synthesis of bis-acetal derivatives (i.e., $R_1$=H, $R_2$=alkyl) Markert et. al. in *Tetrahedron Asymm*. Vol. 15, pages 803-806, 2004 report that lithium perchlorate is a superior catalyst.

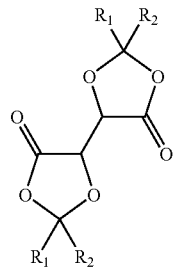

C

Although there is no report of the conversion of C to A in the literature, elimination reactions on other systems are reported to proceed in the presence of very strong bases such as lithium diisopropylamide or sodium hydride. For example, Jarosz and Ciunik in *Pol. J. Chem.*, Vol. 72, pages 1182-1190, 1998 used lithium diisopropylamide to effect such an elimination reaction on compound D while Ferezou et. al. in *Bull. Soc. Chim. Fr.*, Vol. 131, pages 865-894, 1994 used sodium hydride to effect an elimination reaction on compound E. However, as will be shown in Example 3 below, neither lithium diisopropylamide nor sodium hydride is effective for the conversion of C to A. Thus, the discovery that nominally weaker potassium-containing bases allow the facile conversion of C to A is clearly unexpected even to one skilled in the art.

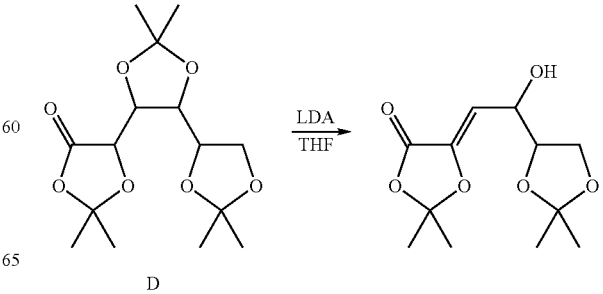

D

-continued

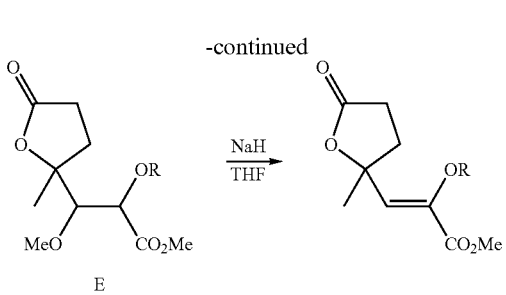

E

BRIEF DESCRIPTION OF THE INVENTION

In accordance with the present invention, a process is provided for preparing a Z-5-carboxymethylene-1,3-dioxolan-4-one of the structure

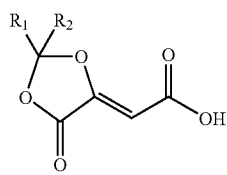

I wherein $R_1$ and $R_2$ may be the same or different and are independently selected from H, lower alkyl or aryl, provided that when one of $R_1$ and $R_2$ is H, the other is H or lower alkyl, which includes the step of treating a bis-ketal or a bis-acetal of tartaric acid having the structure

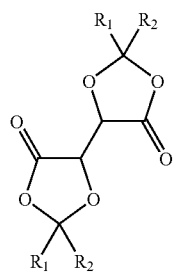

II wherein $R_1$ and $R_2$ are as defined above, with a potassium containing base to form the Z-5-carboxymethylene-1,3-dioxolan-4-one.

It will be appreciated that the $R_1$ and $R_2$ substituents on the compound II will be stable toward treatment with the potassium-containing base. Therefore, compounds of formula II where one of $R_1$ and $R_2$ is H and the other is aryl are excluded.

In addition, in accordance with the present invention, a process is provided for preparing an HIV integrase inhibitor of the structure

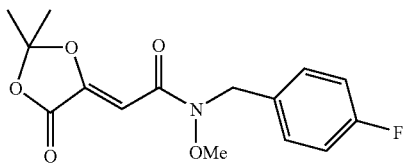

III employing the intermediate of the structure I prepared by the process of the invention, which includes the steps of a. reacting tartaric acid bis(acetonide) of the structure IIA

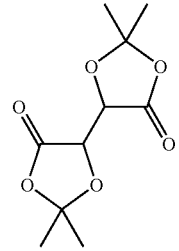

IIA in anhydrous tetrahydrofuran with a potassium tert-butoxide or potassium hexamethyldisilamide in anhydrous tetrahydrofuran at a temperature within the range from about −35° C. to about −45° C. to form Z-2,2-dimethyl-5-carboxymethylene-1,3-dioxolan-4-one of the structure IA

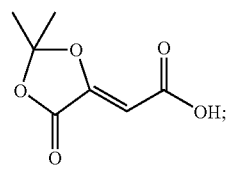

IA b. reacting Z-2,2-dimethyl-5-carboxymethylene-1,3-dioxolan-4-one (IA) with a coupling reagent such as oxalyl chloride (as described in Method C of WO 2004/004657), Vilsmeier reagent or isobutylchloroformate, preferably Vilsmeier reagent or oxalyl chloride, to form the corresponding acid chloride IV

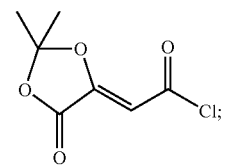

IV and c. reacting the acid chloride with a compound of the structure V

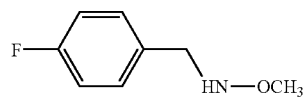

V to form

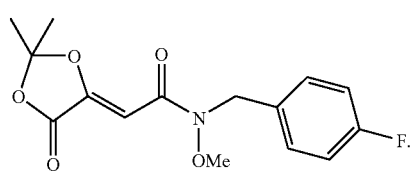

III

A full disclosure of the use of the formula IA intermediate and compound V in the preparation of the formula III HIV integrase inhibitor is disclosed in WO 2004/004657, especially Method C and Example 44 thereof, the disclosure of which is incorporated herein by reference.

DETAILED DESCRIPTION OF THE INVENTION

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl (tricycloalkyl), containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl, adamantyl,

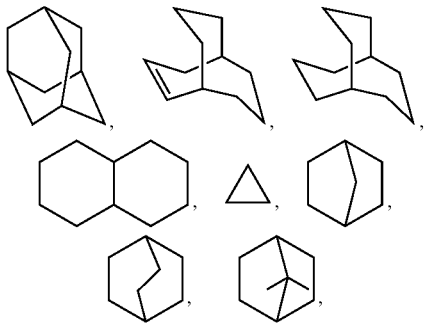

any of which groups may be optionally substituted with 1 to 4 substituents such as halogen, alkyl, alkoxy, hydroxy, aryl, aryloxy, arylalkyl, cycloalkyl, hydroxyalkyl, alkylamido, alkanoylamino, oxo, acyl, arylcarbonylamino, amino, nitro, cyano, thiol and/or alkylthio and/or any of the substituents for alkyl.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

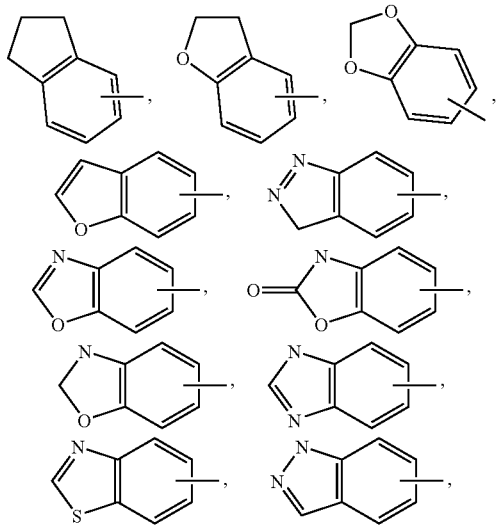

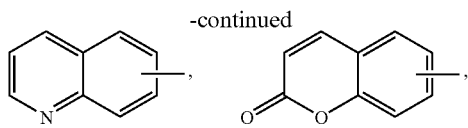

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as:

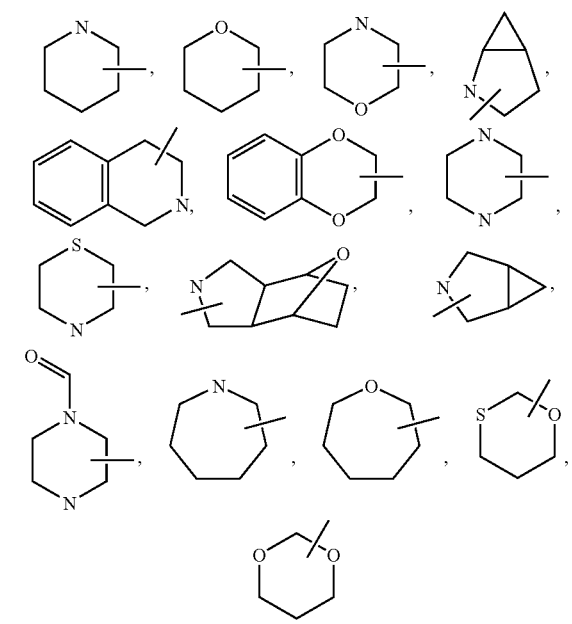

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

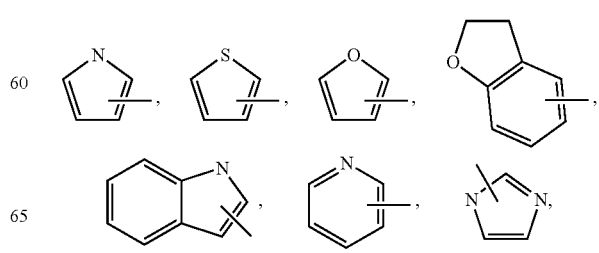

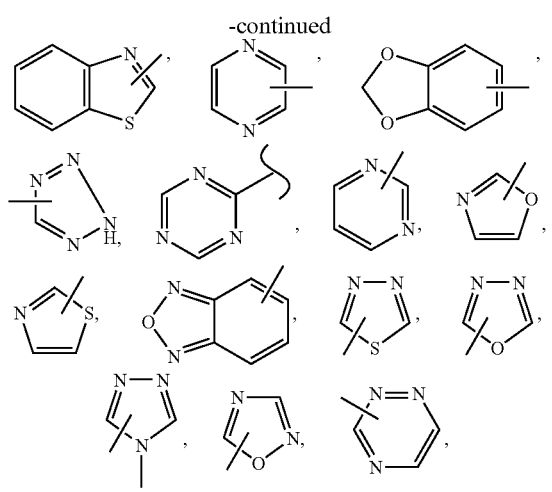

and the like.

The term "cycloheteroalkylalkyl" as used herein alone or as part of another group refers to cycloheteroalkyl groups as defined above linked through a C atom or heteroatom to a $-(CH_2)_r$- chain.

The term "heteroarylalkyl" or "heteroarylalkenyl" as used herein alone or as part of another group refers to a heteroaryl group as defined above linked through a C atom or heteroatom to a $-(CH_2)_r$- chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

In accordance with the process of the present invention, the bis-ketal or bis-acetal of formula II is contacted with a potassium containing base in a suitable solvent to effect an elimination reaction affording the product of formula I directly.

The potassium containing base will be employed in a molar ratio to the bis-ketal or bis-acetal of formula II within the range from about 0.8:1 to about 1.1:1, preferably from about 0.9:1 to about 1.0:1.

Suitable bases for use in the process of the invention are potassium-containing bases such as alkoxides or dialkylamides in which the conjuguate acid has a $pK_a$ higher than about 16. Examples of suitable bases include, but are not limited to, potassium tert-butoxide, potassium tert-amyloxide, potassium hexamethyldisilamide, and potassium diisopropylamide. Alternatively, the base may be generated in situ by the action of potassium hydride on a conjugate acid with a $pK_a$ higher than about 16 such as an alcohol or dialkylamine.

Suitable solvents for use in the process of the invention are those in which both the reactant of formula II and the potassium-containing base are soluble. Both aprotic and protic solvents can be used provided that the $pK_a$ of any protic solvent is not lower than about 16. Suitable solvents include, but are not limited to, 1,2-dimethoxyethane, tert-butyl alcohol, tert-amyl alcohol, dimethylformamide, and tetrahydrofuran, with the latter solvent being especially preferred.

The reaction of compound II and the potassium containing base may be carried out at a temperature within the range from about −80° C. to about +25° C. A reaction temperature within the range from about −60° C. to about −20° C. is preferred and most preferred is a reaction temperature within the range from about −35 to about −45° C.

The starting material for the process of preparing Z-5-carboxymethylene-1,3-dioxolan-4-ones I in accordance with the present invention is a bis-ketal or bis-acetal of tartaric acid having the formula II. These compounds can be prepared by techniques well known to those of ordinary skill in the art. In general, these procedures involve contacting tartaric acid with a ketone or aldehyde in the presence of an acid catalyst and optionally a dehydrating agent. For illustrative purposes, the preparation of tartaric acid bis(acetonide), which has the formula IIA is given as Example 1 below.

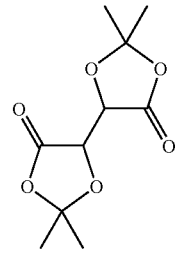

IIA

The Z-5-carboxymethylene-1,3-dioxolan-4-ones represented by formula I are intermediates in the preparation of HIV integrase inhibitors, useful in the treatment of HIV. The syntheses of such HIV integrase inhibitors and their use are disclosed in WO 2004004657, the disclosure of which is incorporated herein by reference.

It is understood that various other embodiments and modifications in the practice of the invention will be apparent to, and can be readily made by, those of ordinary skill in the art without departing from the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the relevant art. The invention is further described with reference to the following experimental work.

EXAMPLES

The following Examples represent preferred embodiments of the invention.

Example 1

Preparation of 2,2,2',2'-tetramethyl-[4,4']bis[[1,3]dioxolanyl]-5,5'-dione

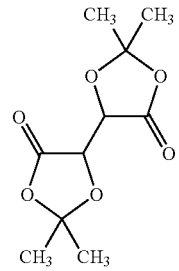

IIA

A glass reactor was charged with L-tartaric acid (1.0 kg), acetone (10.0 L), 2,2-dimethoxypropane (6.5 L), and boron trifluoride diethyletherate (20.0 mL). The mixture was heated at 50° C. for 3 h and then concentrated to a volume of 5 L at reduced pressure in order to remove byproduct methanol and drive the equilibrium. A second charge of acetone (8.0 L) and 2,2-dimethoxypropane (2.0 L) was added; the mixture was heated to 50° C. for 30 min and again concentrated to 5 L. This process was repeated with a third charge of acetone (7.0 L) and 2,2-dimethoxypropane (3.0 L) whereupon the solvent was replaced with methyl tert-butyl ether (5 L). The mixture was quenched by stirring with 8.5% aqueous sodium hydrogen carbonate solution for 30 min. The organic phase was separated. Heptane (5.0 L) was added and the volume was reduced to 5.5 L by vacuum distillation. Additional heptane (12 L) was added to complete the crystallization of the product, which was collected by filtration and washed with heptane (2×2 L). This afforded 2,2,2',2'-tetramethyl-[4,4']bis[[1,3]dioxolanyl]-5,5'-dione (1.13 kg, 74%) as a white crystalline solid.

$^1$H NMR (CDCl$_3$): δ 1.59 (s, 6H), 1.66 (s, 6H), 4.82 (s, 2H). $^{13}$C NMR (dmso-d$_6$): δ 26.5, 26.8, 73.6, 112.1, 169.7.

Example 2

Preparation of Z-2,2-dimethyl-5-carboxymethylene-1,3-dioxolan-4-one

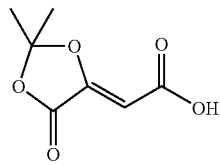

Use of Potassium Tert-Butoxide as Base

A solution of tartaric acid bis(acetonide) prepared as in Example 1 (1.84 g, 8.0 mmol) in anhydrous tetrahydrofuran (15 mL) was cooled to −40° C. A 1 M solution of potassium tert-butoxide in tetrahydrofuran (8.0 mL, 8 mmol) was added by syringe over the course of 5 min. The mixture was stirred an additional 20 min. at −40° C. after which 4 M HCl in dioxane (3.0 mL, 12 mmol) was added and the reaction was allowed to warm. Ethyl acetate (75 mL) and 1 N HCl (25 mL) were added. The organic layer was separated and washed with water (25 mL). Removal of volatiles on the rotary evaporator afforded the crude product (1.37 g, 99%). This material contained ca. 5% of a side-product presumed to be the E-stereoisomer and characterized by an NMR singlet at δ 5.48 as well as ca. 10% of recovered bis(acetonide) starting material. A 0.63 g sample of this material was crystallized from hot ethyl acetate to afford Z-2,2-dimethyl-5-carboxymethylene-1,3-dioxolan-4-one as fine white needles (0.37 g).

$^1$H NMR (dmso-d$_6$): δ 1.74 (s, 6H), 5.58 (s, 1H), 12.62 (br s, 1H). $^{13}$C NMR (dmso-d$_6$): δ26.3, 95.9, 114.9, 147.4, 162.3, 165.2.

Example 3

Preparation of Z-2,2-dimethyl-5-carboxymethylene-1,3-dioxolan-4-one

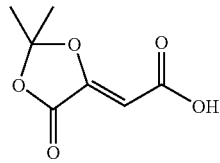

Use of Potassium Hexamethyldisilamide as Base

A solution of tartaric acid bis(acetonide) prepared as in Example 1 (0.46 g, 2.0 mmol) in anhydrous tetrahydrofuran (5 mL) was cooled to −40° C. A solution of potassium bis(trimethylsilyl)amide (0.40 g, 2.0 mmol) in tetrahydrofuran (4.0 mL) was added by syringe over the course of 5 min. The mixture was stirred an additional 20 min. at −40° C. after which 4 M HCl in dioxane (1.0 mL, 4 nmol) was added and the reaction was allowed to warm. Extractive work-up and NMR analysis as in Example 2 indicated that the elimination had proceeded to 70% conversion.

Experiment 1

Comparison Example Showing Ineffectiveness of Lithium Diisopropylamide

A solution of lithium diisopropylamide was generated by addition of 1.6 M butyllithium in hexanes (5.0 µL, 8.0 mmol) to a solution of diisopropylamine (0.85 g, 8.4 mmol) in tetrahydrofuran (15 mL) at −78° C. The resulting solution was added to a stirred solution of tartaric acid bis(acetonide) (1.84 g, 8.0 mmol) in 4.0 mL tetrahydrofuran −78° C. The bath was allowed to warm to −15° C. over the course of 1.5 h. The reaction was quenched by addition of 4 M HCl in dioxane (4.0 mL, 16 mmol). Extractive work-up and NMR analysis as in Example 2 revealed a residue that was overwhelmingly unreacted starting material.

Experiment 2

Comparison Example Showing Ineffectiveness of Sodium Hydride

To a stirred suspension of sodium hydride (0.10 g, 4.2 mmol) in tetrahydrofuran was added a solution of tartaric acid bis(acetonide) prepared as in Example 1 (0.46 g, 2.0 mmol) in tetrahydrofuran (5.0 mL). The mixture was stirred at room temperature for 2 h and was filtered to remove unreacted sodium hydride. Extractive work-up and NMR analysis as in Example 2 revealed a residue that contained only unreacted starting material.

Example 4

Preparation of Z-2,2-dimethyl-5-carboxymethylene-1,3-dioxolan-4-one

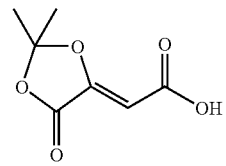

Kilogram Scale Synthesis of I [R$_1$=R$_2$=methyl]

A stirred solution of tartaric acid bis(acetonide) prepared as in Example 1 (1.0 kg) in tetrahydrofuran (5.0 L) was cooled to −40° C. A chilled 0.75 M solution of potassium tert-butoxide in tetrahydrofuran (7.0 L) was added and stirring was continued for 15 min at −40° C. In a separate reactor, a 1.2 M solution of HCl was generated by reaction of acetyl chloride (0.50 L) with methanol (0.31 L) in tetrahydrofuran (5.0 L) 0-5° C. The original reaction is quenched by addition of the chilled HCl solution. The mixture was allowed to warm to room temperature with stirring over the course of 1 h, after which the THF content was reduced to <2% by vacuum distillation. Ethyl acetate (20 L) was added and the mixture was concentrated to 10 L. Deionized water (8.0 L) was added and the pH was adjusted to <2.5 with 1 N HCl. The organic phase was separated and the aqueous phase was further extracted with ethyl acetate (5.0 L). The combined organics were concentrated to a volume of 3 L by vacuum distillation whereupon heptane (6.0 L) was added. The product mixture was vigorously agitated at 15° C. for 1 h after which the crystalline product was collected by filtration and washed with heptane (2×2.0 L). Vacuum drying at 50° C. afforded Z-2,2-dimethyl-5-carboxymethylene-1,3-dioxolan-4-one (577 g, 77%) as fine white needles. NMR and HPLC analysis indicated the product purity was 100%.

Example 5

Preparation of HIV Integrase Inhibitor III

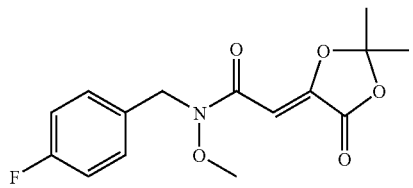
III

The following examplifies the use of intermediate IA (prepared in accordance with the present invention) in preparing the title HIV integrase inhibitor as disclosed in WO 2004/004657.

The following procedure is described in Method C of WO 2004/004657. Please note that the formula IA compound employed was prepared by the process of the present invention.

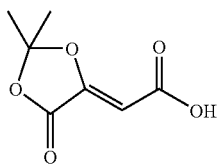
IA

A. (2,2-Dimethyl-5-oxo-[1,3]dioxolan-4-ylidene)-acetyl chloride

A mixture of Z-(2,2-dimethyl-5-carboxymethylene-1,3-dioxolan-4-one (IA) (0.50 g, 2.9 mmol) in dry dichloromethane (10 ml) was treated at 22° C. with oxalyl chloride (0.5 ml, 5.8 mmol) followed by a trace (capillary) of N,N-dimethylformamide. After 1 hr at 22° C., the clear solution was concentrated in vacuo to give 0.55 g (quantitative) of the title acid chloride as a white crystalline solid.

B. 4-Fluoro-benzaldehyde-O-methyl-oxime

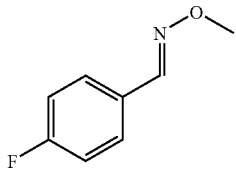

A solution of methoxylamine hydrochloride (13.4 g, 0.16 mol) in a mixture of water (150 ml) and tetrahydrofuran (50 ml) was treated with sodium acetate (11.2 g, 0.136 mol) followed by 4-fluorobenzaldehyde (11.57 g, 93.2 mmol) and the resulting mixture was stirred at 22° C. for 4 hours. The reaction mixture was then diluted with ether, washed with brine and dried over anhydrous magnesium sulfate. Evaporation of the solvent under reduced pressure gave 14.3 g of the crude title material as a clear oil which was used as such for the next step. Distillation of an aliquot in vacuo gave a clear oil; bp 45-50° C./0.5 torr.

$^1$H NMR 400 MHz (CDCl$_3$) δ (ppm):3.99 (3H, s), 7.09 (2H, m), 7.6 (2H, m), 8.06 (1H, s).

C. N-(4-Fluoro-benzyl)-O-methyl-hydroxylamine

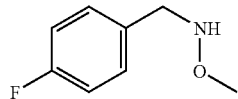

A solution of 4-fluorobenzaldehyde-O-methyloxime (93.2 mmol) in dichloromethane (150 ml) was treated with sodium cyanoborohydride (9.18 g, 0.146 mol) followed by 120 ml of 2 N hydrochloric acid in methanol added dropwise over 30 minutes. After 96 h at 22° C., the solvent was evaporated under reduced pressure and the residue was slurried with water and the pH was adjusted to 9 with 2 N aqueous sodium hydroxide. The aqueous phase was extracted twice with dichloromethane and the combined organic extracts were washed with brine, dried (magnesium sulfate) and concentrated under reduced pressure. The residual oil was chromatographed on silica gel (elution toluene-ethyl acetate 0-10% yield) and gave 5.92 g (41% yield) of the title amine as a clear oil.

$^1$H NMR 400 Mz (CDCl$_3$) δ (ppm):3.49 (3H, s), 4.01 (2H, s), 5.69 (1H, broad s), 7.01 (2H, m), 7.31 (2H, m). The hydrochloride salt was obtained as a white solid: mp 170-171° C. Anal. calcd for C$_8$H$_{10}$FNO—HCl: C, 50.14; H, 5.78; N, 7.31. Found: C, 50.31; H, 5.80; N, 7.26.

D. 2-(2,2-Dimethyl-5-oxo-[1,3]dioxolan-4-ylidene)-N-(4-fluoro-benzyl)-N-methoxy-acetamide III

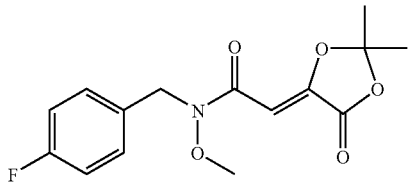
III

A 250 mL flask was charged with Z-(2,2-dimethyl-5-carboxymethylene-1,3-dioxolan-4-one (IA) (10.0 g) (prepared in accordance with the present invention) and Vilsmeier Reagent (9.0 g, Aldrich, 95%) under nitrogen blanket. Then ethyl acetate solvent (135 mL, B&J, high purity) was added and stirred at room temperature for 30 to 60 min to complete the acid chloride formation. The resulting solution was then added to a mixture of N-(4-fluorobenzyl)-O-methyl-hydroxylamine (amine)/ethyl acetate (EA) solution (44 ml of a 246 mg amine/mL EA) and potassium carbonate aqueous solution (103 mL, 20% wt) at 0-5° C. and stirred for 30 min to complete the coupling reaction. The organic layer was separated and washed with 1 N HCl (50 mL) and deionized (d.i.) water (50 mL) and solvent-swapped to isopropyl alcohol by distillation. The product was crystallized at 45 to 50° C. and filtrated at 0° C. and washed with cold isopropyl alcohol (0-5° C.) and heptane and dried in vacuum oven at 50° C. overnight as white crystals (14.55 g, 81%).

The spectral data of the title compound matched the spectral data of an authentic sample and is set out below.

$^1$H NMR (CDCl$_3$): δ 1.75 (s, 6H), 3.68 (s, 3H), 4.79 (s, 2H), 6.38(s, 1H), 7.01 (m, 2H), 7.34 (m, 2H). $^{13}$C NMR (C$_6$D$_6$): δ 27.43, 498.94, 63.62, 110.09, 114.89, 116.21, 131.13, 132.69, 147.59, 161.37, 163.09, 164.95.

What is claimed is:

1. A process for preparing a Z-5-carboxymethylene-1,3-dioxolan-4-one of the structure

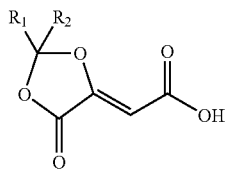

wherein $R_1$ and $R_2$ may be the same or different and are independently selected from H, lower alkyl or aryl provided that when one of $R_1$ and $R_2$ is H, the other is H or lower alkyl, which comprises treating a bis-ketal or bis-acetal of tartaric acid having the structure

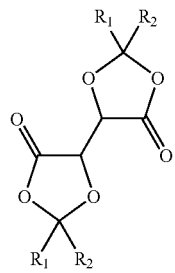

wherein $R_1$ and $R_2$ are as defined above, with a potassium-containing base to form the Z-5-carboxymethylene-1,3-dioxolan-4-one.

2. The process as defined in claim 1 wherein $R_1$ and $R_2$ are the same or different and are lower alkyl.

3. The process as defined in claim 1 wherein $R_1$ and $R_2$ are each $CH_3$.

4. The process as defined in claim 1 wherein the bis-ketal or bis-acetal of tartaric acid is contacted with the potassium base in an organic solvent.

5. The process as defined in claim 1 wherein the potassium-containing base is a potassium alkoxide or a potassium dialkylamide in which the conjugate acid has a $pK_a$ higher than about 16.

6. The process as defined in claim 5 wherein the potassium containing base is potassium tert-butoxide, potassium tert-amyloxide, potassium hexamethyldisilamide or potassium diisopropylamide.

7. The process as defined in claim 1 wherein the potassium containing base is generated in situ by the action of potassium hydride on a conjugate acid with a $pK_a$ higher than about 16 which is an alcohol or a dialkylamine.

8. The process as defined in claim 4 wherein the solvent is 1,2-dimethoxyethane, tert-butyl alcohol, tert-amyl alcohol, dimethylformamide or tetrahydrofuran.

9. The process as defined in claim 1 wherein the reaction between the bis-ketal or bis-acetal of tartaric acid and the potassium containing base is carried out at a temperature within the range from about −80° C. to about +25° C.

10. The process as defined in claim 9 wherein the reaction is carried out at a temperature within the range from about −60° C. to about −20° C.

11. The process as defined in claim 1 wherein the bis-acetal of tartaric acid is prepared by reacting L-tartaric acid, acetone, 2,2-dimethoxypropane and boron trifluoride diethyletherate to form tartaric acid bis(acetonide).

12. A process for preparing Z-2,2-dimethyl-5-carboxymethylene-1,3-dioxolan-4-one having the structure

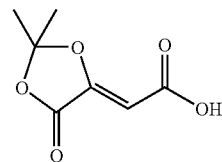

which comprises reacting tartaric acid bis(acetonide) of the structure

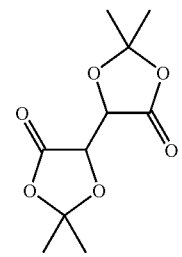

in anhydrous tetrahydrofuran with a potassium-containing base which is potassium tert-butoxide or potassium hexamethyldisilamide in anhydrous tetrahydrofuran at a temperature within the range from about −35° C. to about −45° C. to form Z-2,2-dimethyl-5-carboxymethylene-1,3-dioxolan-4-one.

13. A process for preparing a compound of the structure

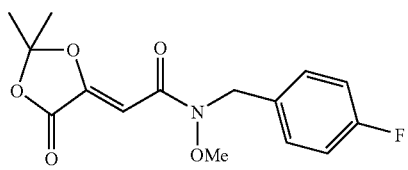

which comprises reacting Z-2,2-dimethyl-5-carboxymethylene-1,3-dioxolan-4-one of the structure

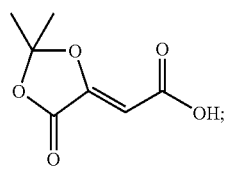

with a coupling agent to form the corresponding acid chloride of the structure

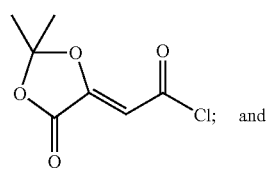

and reacting the acid chloride with a compound of the structure

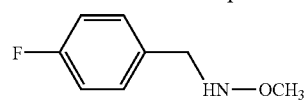

to form

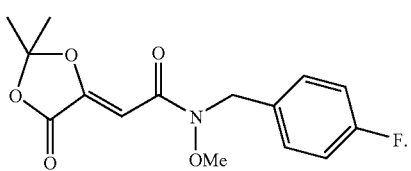

14. The process as defined in claim 1 wherein $R_1$ and $R_2$ are each lower alkyl.

15. The process as defined in claim 1 wherein $R_1$ and $R_2$ are each $CH_3$.

16. A process for preparing

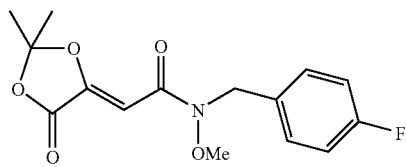

which comprises
  a. reacting tartaric acid bis(acetonide) of the structure

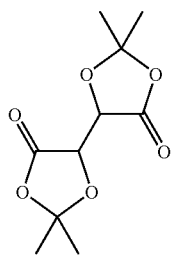

in anhydrous tetrahydrofuran with potassium tert-butoxide or potassium hexamethyldisilamide in anhydrous tetrahydrofuran at a temperature within the range from about −35° C. to about −45° C. to form Z-2,2-dimethyl-5-carboxymethylene-1,3-dioxolan-4-one of the structure

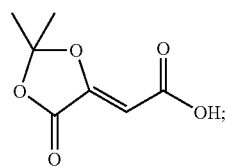

b. reacting the Z-2,2-dimethyl-5-carboxymethylene-1,3-dioxolan-4-one with a coupling agent to form the corresponding acid chloride of the structure

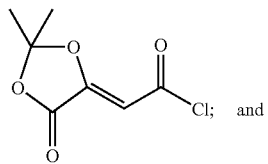 and c. reacting the acid chloride with a compound of the structure

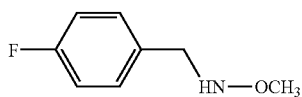

to form

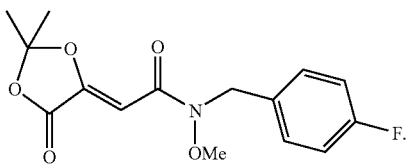

\* \* \* \* \*